US010470959B2

(12) United States Patent
Le

(10) Patent No.: US 10,470,959 B2
(45) Date of Patent: Nov. 12, 2019

(54) SURGICAL MASK POSITIONING SYSTEM

(71) Applicant: Mizhuo Orthopedic Systems, Inc., Union City, CA (US)

(72) Inventor: Peter Le, Union City, CA (US)

(73) Assignee: MIZUHO ORTHOPEDIC SYSTEMS, INC., Union City, CA (US)

( * ) Notice: Subject to any disclaimer, the term of this patent is extended or adjusted under 35 U.S.C. 154(b) by 347 days.

(21) Appl. No.: 15/412,922

(22) Filed: Jan. 23, 2017

(65) Prior Publication Data

US 2018/0207045 A1 Jul. 26, 2018

(51) Int. Cl.
*A61B 6/04* (2006.01)
*A61G 13/12* (2006.01)

(52) U.S. Cl.
CPC ....... *A61G 13/121* (2013.01); *A61G 13/1295* (2013.01); *A61G 2200/325* (2013.01)

(58) Field of Classification Search
CPC .... A61G 13/121; A61G 13/122; A61G 13/04; A61G 15/125; A61G 13/12; A61G 13/1235; A61G 13/1245; A61G 13/1295; A61F 5/055; A61F 5/3707; A61F 5/05883; A61F 13/12; A61F 5/56; A61F 2007/0001; A61F 2007/0002; A61F 5/3723; A61F 5/3776; A61F 5/3715; E05B 75/00; A47C 15/008
See application file for complete search history.

*Primary Examiner* — Ophelia A Hawthorne
(74) *Attorney, Agent, or Firm* — Reed Smith LLP; Matthew P. Frederick; Sidharth Kapoor

(57) ABSTRACT

A positioning system for a surgical mask utilizing an adjustable leg that is positioned on a mirror by way of a series of orifices. The adjustable leg includes a handle rotatably confined by the mirror orifice to raise and lower the surgical mask.

10 Claims, 4 Drawing Sheets

SURGICAL MASK POSITIONING SYSTEM

BACKGROUND OF THE INVENTION

The present invention relates to a novel positioning system for a surgical mask used during surgical procedure.

Certain surgical procedures require a patient to lie in a prone position. For example, spinal surgery is typically under-taken with an anesthetized patient in such prone position on a surgery table.

It is most important that a uniform pressure be applied over the patients face for such prone-position patients. Reduction of tissue pressures on the forehead and chin of an anesthetized prone-position patient eliminates the possibility of damage to the eyes of the patient, for example, central retinol artery occlusion "CRAG". In addition, the patient's head should be maintained in a neutral forward position without significant neck flexion, extension, lateral flexion, or rotation to permit the application of spinal surgery maneuvers. In addition, localized ischemia may occur to the chin and forehead area of the patients head if pressure to those areas is not controlled.

Thus, the need for adjustment of the angle and height of a surgical head support is most important.

In the past, many systems have been proposed to support the head of a person in a supine or prone position. For example, U.S. Pat. Nos. 2,107,962 and 2,239,003 show pillow supports and head rest with adjustable supporting legs.

U.S. Pat. No. 6,023,801 describes a therapeutic head rest for use during medical treatment which includes four adjustable legs supporting a padded cradle.

U.S. Pat. Nos. 4,504,050 and 5,165,137 illustrate head supports used during medical imaging procedures that include angular rotation slotted angular supports as well as adjustable legs for the support platform.

U.S. Pat. Nos. 7,426,763, 8,261,385, and 8,549,683 teach surgical head supports utilizing a shell with a cushion insert positioned above a mirrored surface. The mirrored surface includes adjustable legs extending downwardly therefrom or about the periphery of the mirror.

A product sold under the designation PRONE VIEW utilizes a shell helmet for holding a cushion in which a plurality of threaded member extend up from a mirror surface to engage bosses or extensions of the protective helmet. This arrangement allows the adjustment of the helmet shell, although the shell must be lifted onto the extending legs to secure the same for use.

A positioning system for a surgical mask that includes a positioning system that is accurate and easy to implement would be a notable advance in the medical field of surgical procedures.

SUMMARY OF THE INVENTION

In accordance with the present invention a novel and useful device for positioning a surgical mask above a surface is herein provided.

The device of the present invention utilizes a conventional surgical mask having at least one boss extending therefrom. One or more adjustable support legs are also provided in the present invention. Each support leg includes a first threaded element having a connector fixing the same to the boss extending from the surgical mask. The first threaded element may be fixed by any known connectors such as, screws, lamps, and the like. However, in certain cases the first threaded element may be fixed to the boss extending from the surgical mask by the use of a connector in the form of a mastic or glue. This type of connector is especially advantageous when the boss extending from the surgical mask comprises a hollow member.

The adjustable support leg also includes a second threaded element which adapted for rotatable and threadingly engages the first threaded element. The second threaded element during such engagement is extendable or movable relative to the first threaded element. In certain cases, the first threaded element may take the form of a hollow internally threaded configuration, while the second threaded element may take the form of an externally threaded element. In any case, the second threaded element is moveable relative to the first threaded element by rotation or turning.

The adjustable support leg also is provided with a rotatable handle. The rotatable handle is fixed to the second threaded element for rotation or turning with the second threaded element. The rotatable handle is provided with a body that may include a curved outer surface. Also, a protuberance or projection entails part of the rotatable handle and extends away from the fixed second threaded member.

A mirror is also employed in the present invention and is positioned adjacent the adjustable support leg. The mirror possesses a perimeter, a reflective surface, and an orifice therethrough which lies inwardly from the perimeter. The protuberance of the rotatable handle is extendable into the mirror orifice and is capable of rotation relative to the mirror in this position.

The body of the rotatable handle remains at or above the reflective surface of the mirror during rotation of the rotatable handle body and protuberance. Rotation of the rotatable handle causes movement of the second threaded member relative to the surgical mask, essentially adjusting the position of the surgical mask relative to the reflective surface of the mirror.

Again, a multiplicity of adjustable support legs may be used with the device of the present invention each including the elements of the adjustable support leg described above. In this manner, multiple support legs are independently adjustable allowing the support mask to be moved upwardly and downwardly relative to the reflective surface of the mirror, and may also be tilted in this regard.

It may be apparent that a novel and useful device for positioning the surgical mask for use during surgical procedures has been hereinabove described.

It is therefore an object of the present invention to provide a device for positioning a surgical mask for surgical procedures with include an adjustment mechanism which is easily accessed and positioned relative to a reflective surface of a mirror.

Another object of the present invention is to provide a device for positioning a surgical mask for surgical procedures which is easily adapted to prior art surgical mask structures to allow retrofitting of the same.

Another object of the present invention is to provide a device for positioning a surgical mask for surgical procedures which provides superior eye visualization of the patient during surgery.

A further object of the present invention is to provide a device for positioning a surgical mask for surgical procedures that provides optimum pressure distribution at the face of the patient while retaining neutral neck positioning.

A further object of the present invention is to provide a device for positioning a surgical mask for surgical procedures that may be easily cleaned with standard disinfectants.

The invention possesses other objects and advantages especially as concerns particular characteristics and features thereof which will become apparent as the specification continues.

The following drawings should be considered when determining aspects of the surgical mask positioning device herein provided.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present device will become apparent for the following detailed description of the preferred embodiments thereof. Such embodiments should be referenced to the prior described drawings to fully understand the device sought for patenting.

Figure 1:
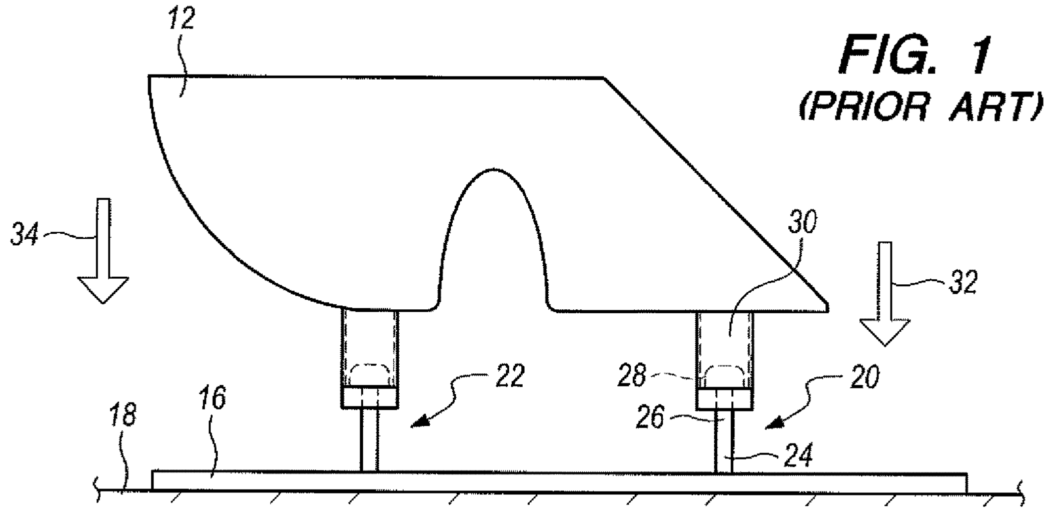
FIG. 1 (PRIOR ART)
FIG. 1 is a side elevational view of a prior art positioning device for a surgical mask.
Figure 2:
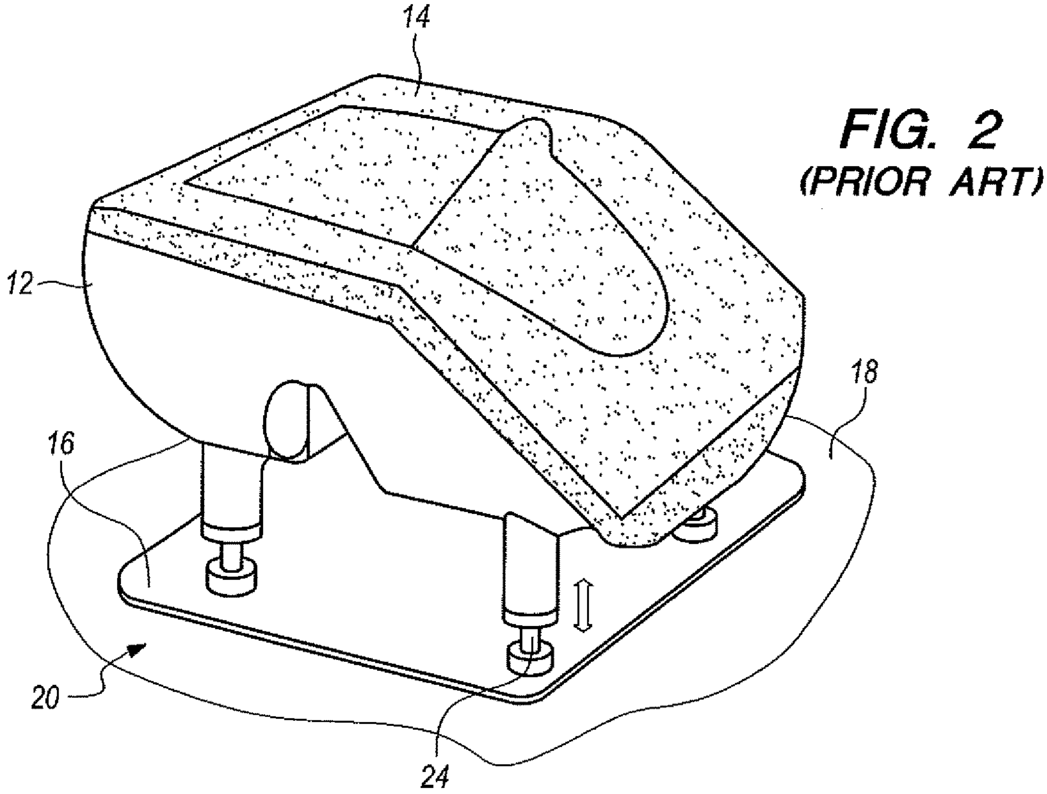
FIG. 2 (PRIOR ART)
FIG. 2 is a top right side prospective view of the device of FIG. 1 showing the surgical mask shell with a foam cushion insert.
Figure 5:
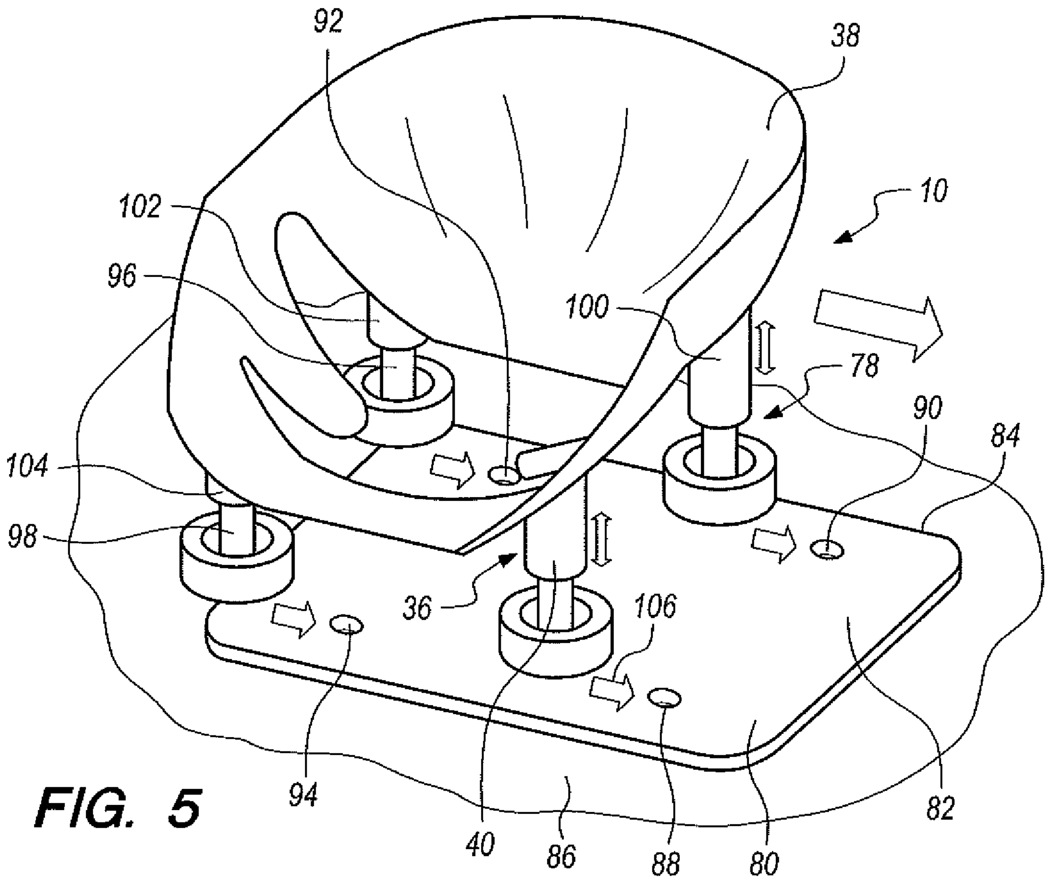
FIG. 5 is a top right side prospective view of a surgical mask using a pair of adjustable legs atop a mirror possessing orifices.
Figure 6:
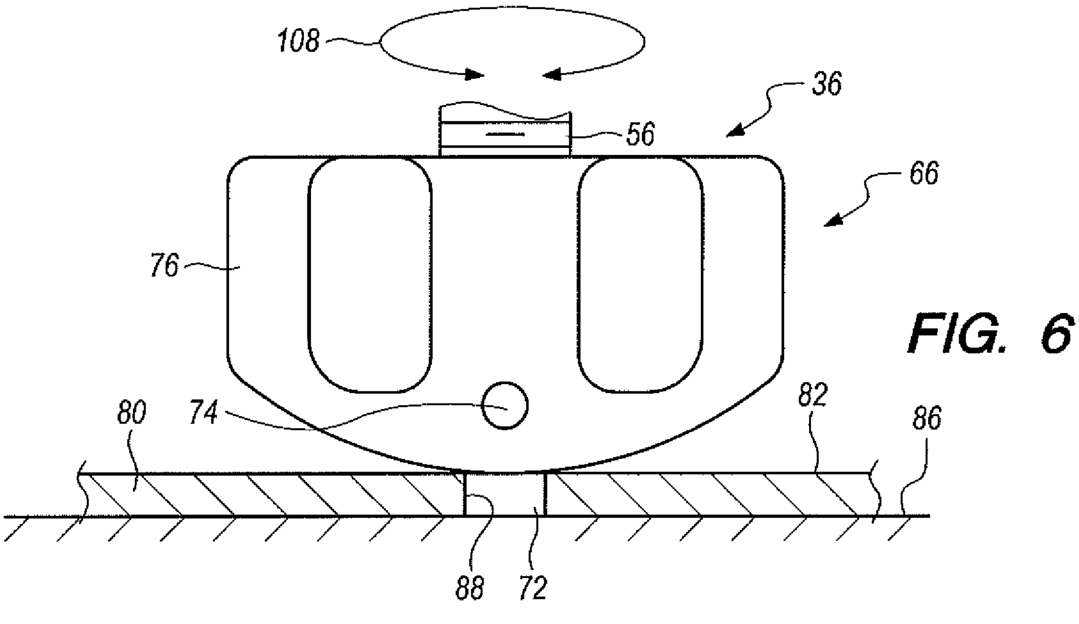
FIG. 6 is an enlarge view of the rotatable handle portion of the device of the present application in which the protuberance has engaged an orifice found in the mirror.

The device of the present invention is shown in the drawings by reference character 10, FIGS. 3-6. Referring to FIGS. 1 and 2, it may be observed that prior art positioning mechanisms for surgical mask 12, such as the PRONEVIEW product, is shown. Prior art mask 12 is depicted in FIG. 2 as including a soft foam liner or insert 14 and is supported above a mirror 16. Mirror 16 lies above a surface 18 which may be the top portion of a surgery table. A plurality of adjustable legs 20 fixed to mirror 16 allow the movement of surgical mask 12 away from and toward mirror 16. Surgical mask 12 also includes a plurality of bosses 22 which engage adjustable legs 20. With reference to adjustable leg 24, typical of the plurality of adjustable legs 20, an upwardly projecting rotatable screw 26 engages a threaded cap 26 placed within boss 30. To operate the adjustment mechanism of adjustable legs 20, surgical mask 12 must be lifted above mirror 16 and placed upon the projecting screws, such as screw 26, of each adjustable leg 20 in order to allow the threaded caps, such as cap 28 of adjustable leg 24, to engage each one of the plurality of bosses 22. Directional arrows 32 and 34 indicate the from adjustable legs 36, 78, 96, and 98 as needed to allow the surgeon to observe the eye area of the head of a patient lying within surgical mask shell 38 atop an foam liner (not shown) in FIG. 5. Once in place, surgical mask shell 38 may be adjusted by turning handle 66 of adjustable leg 36 as well as comparable handles for adjustable legs 78, 96, 98. In other words, surgical mask shell 38 moves up and down, or tilts, relative to mirror 80 as needed. FIG. 6 indicates the turning of handle 66, directional arrow 108, to effect the movement of exemplary adjustable leg 36. Rounded outer body portion 70 of rotatable handle 66 facilitates the turning of handle 66, FIG. 6.

While in the foregoing, embodiments of the present device have been set forth in considerable detail for the purposes of making a complete disclosure of the device, it may be apparent to those of skill in the art that numerous changes may be made in such detail without departing from the spirit and principles of the invention.

downward placement of surgical mask 12 on plurality of adjustable legs 20 via plurality of bosses 22.

Figure 3:
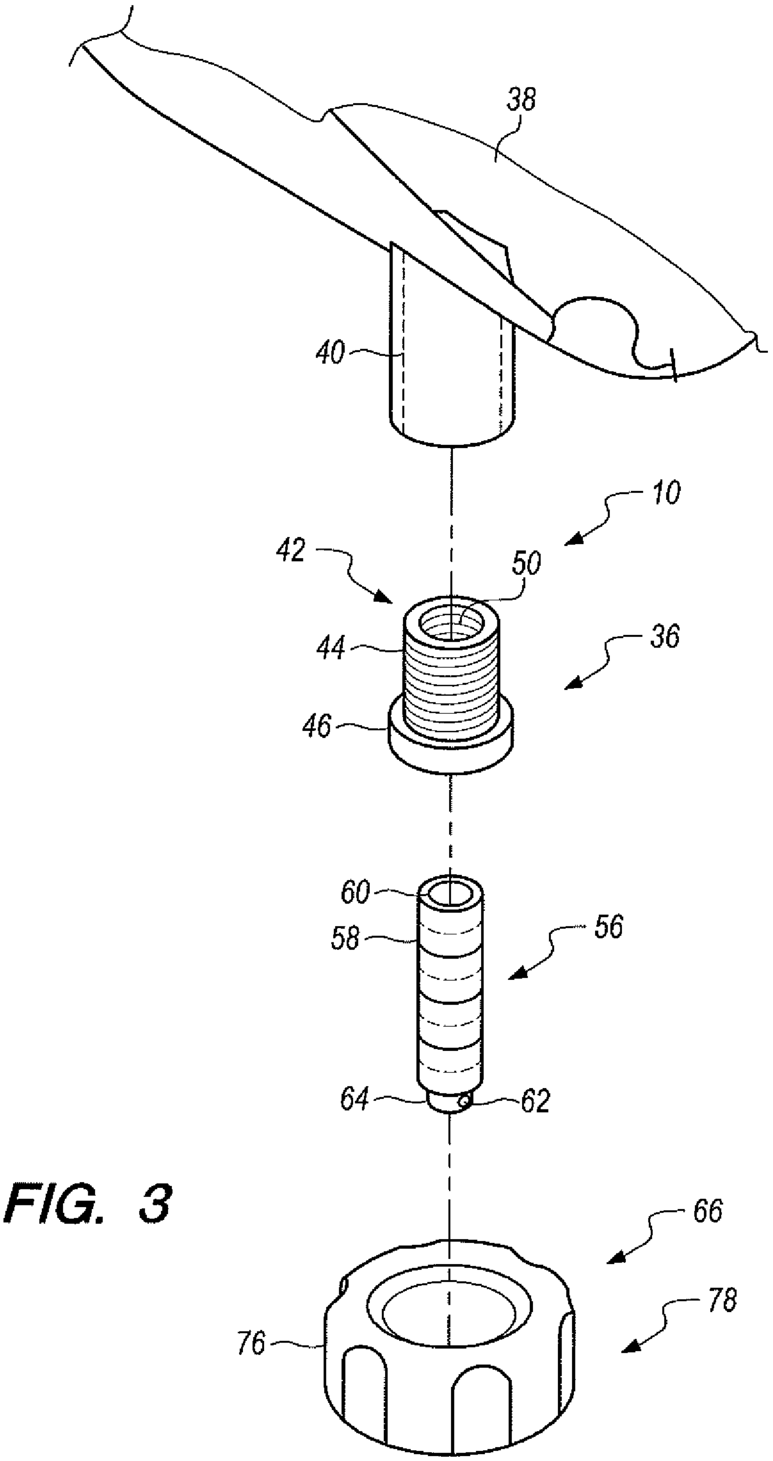
FIG. 3 is an exploded view of the adjustable leg of the present application.
Figure 4:
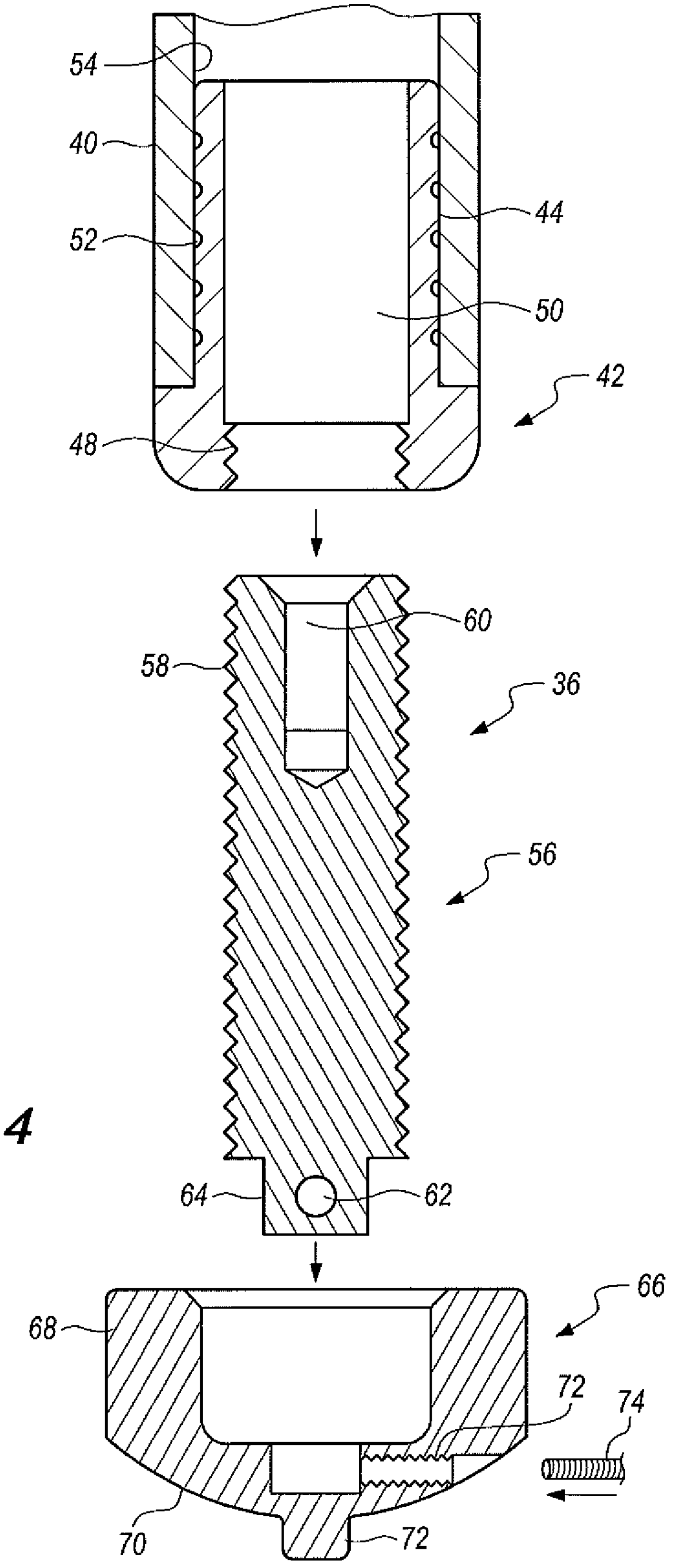
FIG. 4 is a sectional view of the elements depicted in FIG. 3 with the first threaded element attached to the boss of the surgical mask by a mastic.

Looking now at FIG. 3, it may be observed that an exemplary adjustable leg 36 of the present invention is depicted. Conventional surgical mask shell 38, shown partially in FIG. 3, includes an extending boss 40 which is a hollow member of roughly cylindrical shape. Adjustable leg 36 includes as one of its parts a first threaded element 42 having an exterior ribbed surface 44 and a head 46. A thread 48, best shown in FIG. 4, lies within the interior chamber 50 thereof. A connector in the form of a mastic layer 52 positions between rib surface 44 of element 42 and the interior surface 54 of boss 40. Thus, first threaded element 42 is fixed to boss 40 in this regard. Of course after types of connectors may be used to fix first threaded element 42, as heretofore delineated.

In addition, adjustable leg 36 further possesses a second threaded element 56. Second threaded element 56 is provided with an externally threaded surface 58 which is capable of threadingly and rotatably engaging internal threaded surface 48 of first threaded element 42. Of course, the relationship between external threaded surface 58 and internal threaded surface 48 may be reversed such that first threaded element 42 includes an externally threaded surface while second threaded element 56 is provided with an internally threaded surface. In any case, the turning of second threaded element 56 moves the same relative to first threaded element 42, boss 40, and mask 38 fixed thereto. A bore 60 in second threaded element 56 may be employed to receive a filler or cap that may be inserted into bore 60 through surgical mask shell 38. An opening 62 through end portion 64 of second threaded element 56 is intended to interact with rotatable handle 66, more fully described below. Rotatable handle 66 is also provided for in adjustable leg 36.

Rotatable handle 66 includes a body portion 68 with a rounded outer body portion 70. Handle 66 is also fashioned with a protuberance or projection 72. A threaded passageway 74 through body portion 68 of rotatable handle 66 is intended to accept a threaded fastener 74 that engages openings 62 within end portion 64 of second threaded element 56. Opening 62 may also include an internal thread. In any case, second threaded member 56 is secured or fixed to handle 66 in this manner, such that rotation of rotatable handle 66 also turns or rotates second threaded element 56. It should be noted that the outer surface 76 of rotatable handles 66 includes a plurality of recesses 78 to facilitate the gripping of rotatable handle 66 by the user of adjustable leg 36.

Positioning device 10, including adjustable leg 36, may also include an adjustable leg 78 which is constructed in a similar manner to adjustable leg 36. In fact, all the legs 36, 78, 96 and 98 associated with surgical mask shell 38 may include the same adjustment mechanism as that found with respect adjustable leg 36 prior described.

Referring now to FIG. 5, device 10 also utilizes a mirror 80 having an upper reflective surface 82 and a perimeter 84. Mirror 80 is intended to lie above a surface 86 which may be the upper portion of a medical or surgical table. Mirror 80 also includes orifices 88, 90, 92, and 94, aligned with legs 36, 78, 96 and 98. As shown in FIG. 5, legs 96 and 98 associated with surgical mask shell 38 are similarly constructed to adjustable legs 36 and 78. That is to say, a protuberance such as protuberance 72 of rotatable handle 66 of adjustable leg 36, is found on adjustable legs 78, 96, and 98, associated with bosses 100, 102 and 104 of surgical mask shell 38.

In operation, FIG. 5, the user places surgical mask shell 38 atop mirrors reflective surface 82 near orifices 88, 90, 92, and 94. Surgical mask 38 having adjustable legs 36, 78, 96, and 98 rest atop reflective surface 82 of mirror 80. Surgical mask shell 38 is then slid along reflective surface 82 of mirror 80 to allow protuberance 72 of adjustable leg 36 to engage orifice 88 according to directional arrow 106. Simultaneously, protuberances similar to protuberance 72 associates with adjustable legs 78, 96, and 98 engage orifices 90, 92, and 94, respectively. Surgical mask shell 38 is then secure in place atop reflective surface 82 apart from perimeter 84 of mirror 80. Such positioning, as may be seen, takes place without lifting surgical mask 38, and allows the perimeter 84 of reflective surface 82 extend outwardly from adjustable legs 36, 78, 96, and 98 as needed to allow the surgeon to observe the eye area of the head of a patient lying within surgical mask shell 38 atop an foam liner (not shown) in FIG. 5. Once in place, surgical mask shell 38 may be adjusted by turning handle 66 of adjustable leg 36 as well as comparable handles for adjustable legs 78, 96, 98. In other words, surgical mask shell 38 moves up and down, or tilts, relative to mirror 80 as needed. FIG. 6 indicates the turning of handle 66, directional arrow 108, to effect the movement of exemplary adjustable leg 36. Rounded outer body portion 70 of rotatable handle 66 facilitates the turning of handle 66, FIG. 6.

While in the foregoing, embodiments of the present device have been set forth in considerable detail for the purposes of making a complete disclosure of the device, it may be apparent to those of skill in the art that numerous changes may be made in such detail without departing from the spirit and principles of the invention.

What is claimed is:

1. A device for positioning a surgical mask directly above a surface, the surgical mask including at least one boss extending from the surgical mask, the device comprising:

a. an adjustable support leg, said adjustable support leg comprising:
   - a first threaded element, said first threaded element including a connector fixing said first threaded element to the at least one boss;
   - a second threaded element, said second threaded element adapted for rotatably, threadingly engaging said first threaded element, said second threaded element being extendable from said first threaded element;
   - a rotatable handle, said rotatable handle being fixed to said second threaded element for rotation therewith, said rotatable handle including a body and a protuberance extending away from said fixed second threaded element;

b. a mirror, said mirror being positioned adjacent to said adjustable support leg, said mirror including a perimeter, a reflective surface, and an orifice therethrough, placed inward from said perimeter, said protuberance extending into said mirror orifice and being rotatable relative to said mirror, said body of said rotatable handle remaining at or above said reflective surface of said mirror during rotation of said protuberance, said rotation of said rotatable handle causing movement of said second threaded element relative to the surgical mask.

2. The device of claim 1 in which said first threaded element comprises a hollow internally threaded element.

3. The device of claim 1 in which said second threaded element comprises an externally threaded element.

4. The device of claim 1 in which the at least one boss comprises a first boss and a second boss, and where said adjustable support leg comprises a first adjustable support leg and a second adjustable support leg, said second adjustable support leg comprising:

- a first threaded element, said first threaded element including a connector fixing said first threaded element to the second boss;
- a second threaded element, said second threaded element adapted for rotatably threadingly engaging said first threaded element, said second threaded element being extendable from said first threaded element; and
- a rotatable handle, said rotatable handle being fixed to said second threaded element for rotation therewith, said rotatable handle including a body and a protuberance extending away from said second threaded element;
- said mirror orifice comprising a first mirror orifice and a second mirror orifice through said reflective surface of said mirror, placed inward from said perimeter of said mirror, said protuberance of said rotatable handle of said second adjustable support leg extending into said second mirror orifice for rotation relative to said mirror, said body of said rotatable handle of said second adjustable support leg remaining at or above said reflective surface of said mirror during rotation of said rotatable handle of said second adjustable support leg, said rotation of said handle of said second adjustable support leg causing movement of said second threaded element of said second adjustable support leg relative to the surgical mask.

5. The device of claim 4 in which said second threaded element of said second adjustable support leg comprises an externally threaded element.

6. The device of claim 5 in which said connector for fixing said first threaded element of said second adjustable leg support to second boss comprises a mastic.

7. The device of claim 1 in which said body of said rotatable handle comprises a curved outer surface adjacent to said protuberance.

8. The device of claim 1 in which said connector fixing said first threaded element to the at least one boss comprises a mastic.

9. The device of claim 4 in which said first threaded element of said second adjustable support leg comprises an externally threaded element.

10. The device of claim 4 in which said body of said rotatable handle of said second adjustable support leg comprises a curved outer surface adjacent to said protuberance.

* * * * *